United States Patent [19]
Hirata

[11] Patent Number: 5,906,829
[45] Date of Patent: May 25, 1999

[54] POULTICE COMPRISING A TITANIUM-BASED MATERIAL

[75] Inventor: Yoshihiro Hirata, Kyoto, Japan

[73] Assignee: Phild, Co., Ltd., Kyoto Pref., Japan

[21] Appl. No.: 08/822,721

[22] Filed: Mar. 24, 1997

[30] Foreign Application Priority Data

May 13, 1996 [JP] Japan ..................................... 8-154713

[51] Int. Cl.⁶ .................................................. A61F 13/00
[52] U.S. Cl. ........................ 424/443; 424/447; 424/448; 424/449
[58] Field of Search ................... 424/447, 448, 424/449, 443

[56] References Cited

U.S. PATENT DOCUMENTS

| | | | |
|---|---|---|---|
| 4,666,441 | 5/1987 | Andriola | 604/897 |
| 4,699,792 | 10/1987 | Nick | 424/446 |
| 5,204,109 | 4/1993 | Akemi | 424/443 |
| 5,505,956 | 4/1996 | Kim | 424/448 |
| 5,547,681 | 8/1996 | Clark | 424/449 |

*Primary Examiner*—D. Gabrielle Brouillette
*Attorney, Agent, or Firm*—Wenderoth, Lind & Ponack, L.L.P.

[57] ABSTRACT

The present invention provides a material for promoting health and curing bruises, etc., which is able to widely exert favorable influences on symptoms such as contusions, sprains, stiffness of the shoulders, and myosalgia and to cure the same in a short time, wherein a kneaded substance 2 is laminated on one side of base material 1 such as unwoven fabric and the kneaded substance is applied to an affected part. The kneaded substance is produced by kneading a titanium based material 4 and topicum for compress in a gelling agent. The electromagnetic and electric actions which the titanium based material has, and actions of pain killing, sedation, improvement of the blood circulation, and promotion of metabolism are simultaneously made effective, and it is possible to apply the same in a wide range of symptoms and to cure them in a short time.

14 Claims, 2 Drawing Sheets

POULTICE COMPRISING A TITANIUM-BASED MATERIAL

FIELD OF THE INVENTION

The present invention relates to a material for promoting health and curing bruises, etc., which is used in a pattern of poultice or cataplasma.

PRIOR ARTS

A poultice or cataplasma material is prepared by a process in which a topicum such as peppermint oil, methyl salicylate, etc. is kneaded with a gelling agent consisting of kaolin, glycerin, etc. Said poultice material is used by coating the same onto an affected part for the sake of antiphlogistic and pain killing against contusions, sprains, stiffness of the shoulders, and myosalgia.

SUMMARY OF THE INVENTION AND ADVANTAGES

However, as methyl salicylate aims at antiphlogistic and pain killing and peppermint oil aims at promotion of blood circulation, a topicum used for a poultice material has only a limited effect for individual medicines. Therefore, a single poultice or cataplasma material is not able to cure a number of symptoms, and it is necessary to change to a plurality of poultice materials or to knead another topicum according to the symptoms.

Furthermore, such a poultice material will not sufficiently take effect, depending on the symptoms or affected parts, whereby a longer period of time is required to completely cure the symptoms, the number of times of changing such poultice materials is increased, and inflammations may occur on the skin due to such poultice materials. That is, said poultice materials have such inconvenient disadvantages.

The invention was developed in view of such situations, and it is therefore an object of the invention to provide a material for promoting health and curing bruises, etc., which is applicable to a wide range of symptoms and is able to cure the symptoms in a short time.

As described above, a material for promoting health and curing bruises, etc., is able to cause a curing action, by a titanium based material, and a compress action by a topicum, to be exerted onto an affected part at the same time. Therefore, it is possible to apply the same material in a wide range of symptoms and to cure the symptoms in a short time.

BRIEF DESCRIPTION OF THE DRAWINGS

Other advantages of the invention will be readily appreciated as the same becomes better understood by reference to the following detailed description when considered in connection with the accompanying drawings wherein.

DETAILED DESCRIPTION OF THE INVENTION

Figure 1:
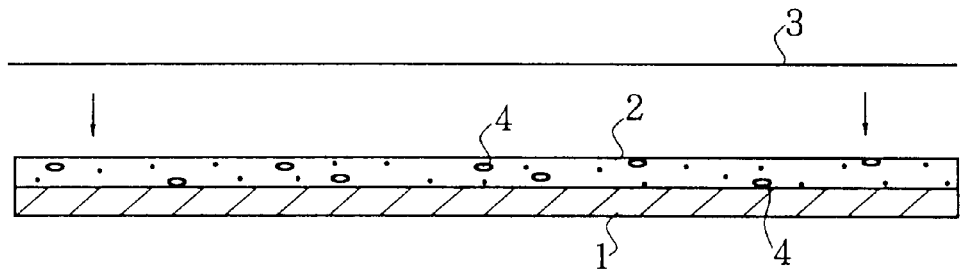
FIG. 1 is a cross-sectional view of a second preferred embodiment of the invention.

In order to achieve the above object, the invention is characterized in that a titanium based material and topicum are kneaded and mixed in a gelling agent.

Said titanium based material has various kinds of actions such as fever absorption, sedation, promotion of the blood circulation and/or metabolism. In a case where said titanium based material is kneaded and mixed with a gelling material along with a topicum and is coated onto an affected part, since the actions of said titanium based material and medical effects of said topicum are efficacious to the affected part, it is possible to cure the affected part in a short time and possible to apply the same to a number of the symptoms.

In another embodiment the invention is characterized by a kneaded substance in which a titanium based material and topicum are kneaded and mixed with a gelling agent and a base material on one side of which said kneaded substance is laminated.

By laminating said kneaded substance onto a base material, they are made integral with each other, and said kneaded substance is applied to an affected part for use in this state. In this use condition, since a base material covers said kneaded substance so as not to allow said kneaded substance to be exposed, no kneaded substance can adhere to clothing, and it is very convenient to use.

In another embodiment the invention is characterized by a kneaded substance in which a topicum is kneaded and mixed with a gelling agent, a base material on one side of which said kneaded substance is laminated; and a titanium based material, the surface of which is disposed to be exposed onto the surface of said kneaded substance.

By said titanium based material being exposed to the surface of said kneaded substance, said titanium based material is directly brought into contact with an affected part. Therefore, the actions of said titanium based material directly and strongly permeate into said affected part, thereby causing said affected part to be cured in a short time.

In another embodiment the invention is characterized by a kneaded substance in which a titanium based material and topicum are kneaded and mixed with a gelling agent, and an adherent substance which has concave parts and has said kneaded substance fills in said concave parts.

The circumferential parts of the concave parts of said adherent material are made to adhere to an affected part, whereby said kneaded substance in said concave parts intensively adheres to the affected part. Therefore, it will not unexpectedly fall off, and a stabilized use can be accomplished, which will be able to contribute to early curing and treatment.

In another embodiment the invention is characterized by a kneaded substance in which a topicum is kneaded and mixed with a gelling agent, an adherent substance which has concave parts and said kneaded substance fills in said concave parts, and a titanium based material, the surface of which is exposed onto the surface of said kneaded substance.

This structure has an action that said titanium based material is directly brought into contact with an affected part and another action resulting from adhering of said adherent material.

In another embodiment the invention is characterized in that the surface of said kneaded substance is covered with a film having a gas barrier property.

By said film of a gas barrier property covering the surface of said kneaded substance, since the water content thereof is prevented from evaporating, the kneaded substance will not dry and will be able to remain effective.

PREFERRED EMBODIMENTS OF THE INVENTION

A first preferred embodiment of the invention is such that a titanium based material and a topicum are kneaded and mixed in a gelling agent and is entirely mud-like and is supplied in an enclosed container.

A topicum may be selected to be anything similar to that kneaded in a general poultice or cataplasma material. Furthermore, said topicum may be adequately selected and employed according to the purpose of a material for promoting health and curing bruises, etc. For example, in a case where the major purpose is antiphlogistic or pain killing, salicylic derivatives such as glycol salicylate, methyl salicylate, and d,1-menthol, etc. may be selected, in a case where the major purpose is promotion of the blood circulation, vitamin E ester acetate, peppermint oil, thymol, etc. may be selected, and in a case where the major purpose is activation of the skin by a stimulus, d,1-camphor, turpentine oil, etc. may be selected. Furthermore, in a case where the major purpose is promotion of metabolism, glycyrrhizin acid, etc. may be used.

It is possible to treat different symptoms by kneading a plurality of topicums having different effects in a gelling agent. Furthermore, a topicum to be kneaded may be selected according to a use pattern of a material for promoting health and curing bruises, etc. For example, in a case of a warm compress, it is possible to add a red pepper extract as a skin stimulant. Furthermore, additives such as paraben, isopropyl methyl phenol, dibutyl hydroxy toluene, rosin ester, etc. may be added thereto. A perfume may also be added. In addition, when it is necessary to increase the adhesivity of a gelling agent, an adhesivity increasing agent such as nonyl acid vanillin etc. may be added.

By adequately selecting topicums described above and kneading the same in a gelling agent, various actions such as pain killing, sedation, improvement of the blood circulation, promotion of metabolism, etc. may be given to a material for promoting health and curing bruises, etc. By coating the same onto an affected part or adhering a gauze to which the same is coated, to the affected part, it is possible to suppress pain and/or fever due to an external wound and acute inflammation such as a bruise, sprain, fracture, etc.

A gelling material is mainly used for adsorption to the skin. Kaoline, starch, linseed powder, etc. may be used as the base material of a gelling agent, and adhesivity increasing agent such as glycerin, etc. may be added thereto. By adding these as the base materials, such a gelling agent will be able to provide various features such as fever absorption, keeping humidity on the skin, tissue softening, and waste matter elimination, etc.

The amount of addition of topicums relative to the gelling agent is adequately changed in compliance with the purpose, place of a material for promoting health and curing bruises, etc, and according to the symptoms. An example of the prescription thereof is shown below. Furthermore, this prescription is for a case where a titanium based material described later is eliminated.

| (Example of prescription) | |
|---|---|
| Kaolin powder | 500 to 600 grams |
| Boracic acid | 40 to 60 grams |
| Concentrated glycerin | 300 to 500 grams |
| Methyl salicylate | 2 ml |
| Peppermint oil | 0.5 ml |
| Thymol | 0.5 grams |
| Total quantity | 1,000 grams |

The boracic acid is added to concentrated glycerin, heated and dissolved. Kaolin powder which is heated to 110° C. or so and treated for sterilization is mixed with the same. After cooling the same, methyl salicylate, peppermint oil, thymol and a titanium based material described later are added to the same and kneaded, whereby a gelling agent is able to be produced.

A titanium based material is a substance, the major component of which is titanium (Ti). Titanium based materials are widely utilized for repair and correcting of teeth and bones in medical and clinical fields. It is known that not only titanium itself is harmless to the human body but also that it has effective physiological actions such as fever absorption, sedation, promotion of the blood circulation and metabolism, etc. Furthermore, titanium is chemically stable, is free from any deterioration and change in quality as time elapses and maintains effectiveness for a longer period of time.

Furthermore, according to the study of the present inventor, it was found that titanium has a slightly electric and electromagnetic action. This electric and electromagnetic action acts upon iron elements in hemoglobin in the blood to make them active.

A titanium based material used in a material for promoting health and curing bruises, etc. is titanium itself, or a titanium compound or titanium alloy including titanium. Among them, as titanium compounds, hydrides such as $TiH_2$, $TiH_4$, etc., oxides such as $TiO$, $Ti_2O_3$, $TiO_2$, $Ti(OH)_2$, $Ti(OH)_3$, $M_2TiO_3$ (M is univalent metal), etc., or their related compounds, sulfides such as $TiS$, $Ti_2S_3$, $TiS_2$, etc., and oxyacid salts such as $Ti_2(SO_4)_3$, $Ti(SO_4)_2$, $TiP_2O_7$, etc. may be used.

Furthermore, as titanium compounds, borates such as $Ti_2B$, $TiB$, $TiB_2$, $Ti_2B_5$, etc., titanium carbide consisting of $TiC$, sulfides such as $TiSi_2$, $TiSi$, $Ti_5Si_3$, etc., nitrides such as $TiN$, $Ti_3N_4$, $Ti_3N_6$, $Ti_5N_6$, etc., and phosphide such as $TiP_n$ may be used.

Still furthermore, compounds of titanium and halogen may be used. For example, $TiCl_2$, $TiCl_3$, $TiCl_4$, $TiBr_2$, $TiBr_3$, $TiBr_4$, $TiI_2$, $TiI_3$, $TiI_4$, etc. may be selected as this halogen compound. In addition, conjugated acids such as $M_2TiF_5$, $M_3TiF_6$, $M_2TiF_6$, $M_2[TiCl_5(OH)_2]$, $M_2TiCl_6$, $[Ti(OH)_6]Cl_3$, $M_2[.TiBr_6]$, etc. may be used.

On the other hand, as a titanium alloy, alloys of titanium and metals such as copper, lead, iron, aluminium, chromium, cobalt, molybdenum, tungsten etc., may be used. Ti—Al, Ti—V, Ti—Mo, Ti—Cr, Ti—Mn, Ti—Fe, Ti—Al—Cr, Ti—Cr—Fe—O, etc. are available as this titanium alloy, and it is possible to optionally select the ratio of composition of the respective alloys.

Anything including titanium may be selected as a titanium based material. Therefore, not only may minerals such as rutile, brookite, anatase, etc. be used, but also, titanium acid chlorides such as $CaTiO_3$, $SrTiO_3$, $BaTiO_3$, $CdTiO_3$, $PbTiO_3$, etc., may be used. Still furthermore, a plurality of titanium based materials may simultaneously be used.

Such a titanium based material is kneaded in a gelling agent in a granular or particle-like form, whereby the titanium based material is able to be uniformly dispersed in a gelling agent by kneading.

In this preferred embodiment, titanium carbide was selected as the titanium based material. This titanium carbide is a compound generated by carbonizing titanium. Titanium carbide still has the abovementioned actions which titanium has. Actually, the present inventor confirmed that titanium carbide has effective physiological actions such as fever absorption, sedation, etc., and electric and electromagnetic actions as titanium.

In addition to having such properties, the chemical and thermal stabilities of titanium carbide are increased more than titanium, by carbonizing titanium. That is, not only does titanium carbonite have the properties which titanium has, but also the properties are not changed as time elapses and remain unchanged, whereby titanium carbide has better medical and clinical properties than just titanium.

As described above, a material for promoting health and curing bruises, etc. in which a topicum and titanium based material are kneaded in a gelling agent, is coated onto a gauze, cloth, unwoven fabric, etc. with an adequate thickness, and the same is applied to an affected part for use. In this use condition, effective physiological actions such as fever absorption, sedation, promotion of blood circulation and metabolism of a titanium based material such as titanium carbide are able to permeate into the human body in addition to the medical efficacy of such a topicum, whereby it is possible to treat and cure a contusion, lumbago, sprain, muscular ache, and other symptoms. Furthermore, since the blood circulation is improved by electric and electromagnetic actions of titanium based material, stiffness of the shoulders is able to be removed along with reducing fatigue. Still furthermore, since the titanium based material has a number of actions as described above, it is possible to apply a material according to the invention to a wide range of the symptoms. Additionally, since a titanium based material effectively maintains those actions for a longer period of time, the number of times for changing the poultice can be decreased, which is very convenient.

FIG. 1 shows a second preferred embodiment which has a base material 1 and a kneaded substance 2 laminated on one side of said base material 1. Said base material 1 may consist of cloth such as unwoven fabric, gauze, etc., flexible resin such as vinyl chloride resin, nylon, or a paper material. Kneaded substance 2 is composed by coating the kneaded substance 2 thereonto with a fixed thickness.

The kneaded substance 2 which is identical to that in the first preferred embodiment is used, granular titanium based material 4 is dispersed inside the kneaded substance 2. 3 is a film with a gas barrier property, which covers the surface of said kneaded substance 2. It is possible to suppress the water evaporation from said kneaded substance 2 by the kneaded substance 2 being covered with said film 3.

In this preferred embodiment, said film 3 is peeled off, and the surface of said kneaded substance 2 is applied to an affected part for use, whereby actions similar to those in the first preferred embodiment are able to be brought on, and it is very convenient to use because the use method is very simple.

Figure 2:
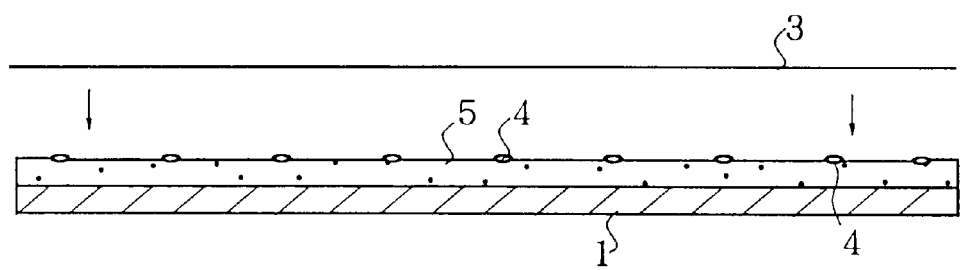
FIG. 2 is a cross-sectional view of a third preferred embodiment of the invention.

FIG. 2 shows a third preferred embodiment of the invention, wherein a base material 1 and film 3 are similar to those in the second preferred embodiment. In this third preferred embodiment, a kneaded substance 5 laminated on one side of said base material 1 is such that only a topicum is kneaded in a gelling agent. That is, when kneading, titanium based material is not kneaded in the gelling agent. The kneaded substance 5 in which only a topicum is kneaded is laminated on the base material 1, and thereafter, a titanium based material 4 is disposed on the surface of said kneaded substance 5.

Such a disposition of titanium based material 4 can be easily carried out by a method that granular titanium based material 4 is sprayed onto the surface of said kneaded substance on the base material 1 and is pressed by using a roller (not illustrated). By this kind of process, the titanium based material 4 is disposed in such a way that the surface thereof is exposed on the surface of said kneaded substance 5.

Therefore, the titanium based material 4 is directly brought into contact with an affected part, whereby actions inherent to the titanium based material directly and intensively permeate into the skin, whereby an early treatment is made possible. Furthermore, since said kneaded substance 5 is brought into contact with an affected part among grains of titanium based material 4, it is similar to the actions of the abovementioned embodiments that the effects of a topicum is exerted on the affected part.

Figure 3:
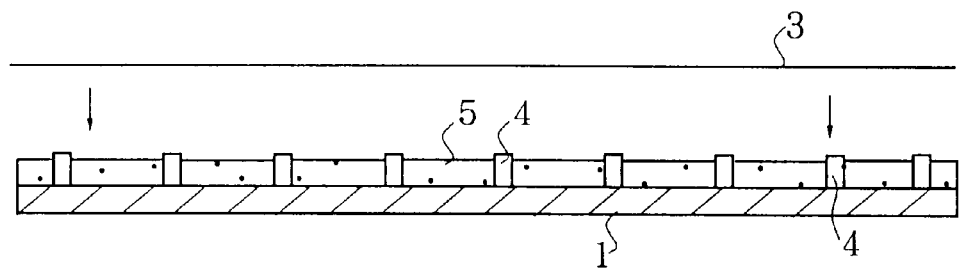
FIG. 3 is a cross-sectional view of a modified example of the third preferred embodiment.

FIG. 3 shows a modified example of the third preferred embodiment, wherein a titanium based material 4 is formed to be like a slender chip. The chip-like titanium based material 4 is such that the lower end face thereof is adhered to the base material 1. The adhering is achieved in such a way that a plurality of titanium based materials 4 are fitted in a punching plate or a fixture such as a meshed body, the lower end of those titanium based materials 4 are brought into contact with the base material 1 in this condition, and they are welded or cemented by ultrasonic waves. Thereby, titanium based materials 4 are disposed to be erect on the base material 1, thereafter a kneaded substance 5 in which a topicum is kneaded in a gelling agent is poured onto the base material 1, whereby the structure shown in FIG. 3 can be achieved.

With this structure, since the upper end face of the titanium based material 4 is exposed from the surface of said kneaded substance 5, the titanium based materials 4 are directly brought into contact with an affected part as in FIG. 2, whereby the actions of titanium based materials 4 are able to intensively permeate into the affected part.

Figure 4:
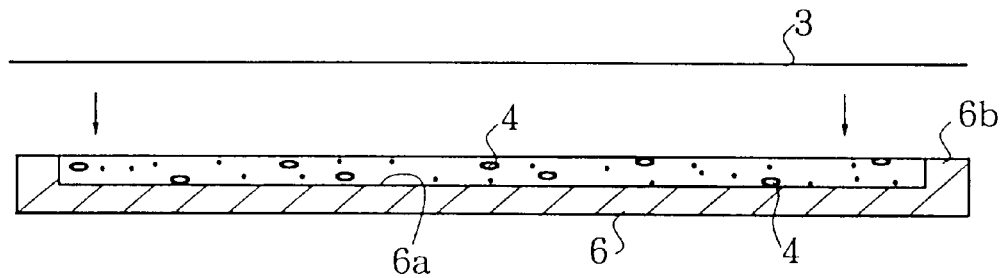
FIG. 4 is a cross-sectional view of a fourth preferred embodiment.

FIG. 4 shows a fourth preferred embodiment, wherein 6 is an adherent base material. Said adherent base material 6 is shaped to be like a disk consisting of concave parts 6a and edge parts 6b which are erect from the circumferential portion of said concave parts 6a, and a kneaded substance 2 which is similar to that in the second preferred embodiment fills these concave parts 6a. That is, the kneaded substance 2 is such that granular titanium based materials 4 and a topicum are kneaded in a gelling agent.

Said adherent base material 6 in this preferred embodiment is made of a mixture of pine tar, mineral oil, etc. with synthetic rubber or natural gum, or of an adhesive agent such as polyacryl acid ester based resin, polyvinyl ether based resin, etc. They have a good adhesion to the skin. The edge portions 6b of the adherent base material 6 are directly brought into contact with the skin, and the base material 6 is able to adhere to the skin by the adhesion thereof.

Therefore, titanium based material 4 and topicum of the kneaded substance 2 filling the concave parts 6a is able to act on an affected part without slipping off. Since it is possible for the titanium based material and topicum to be intensively exerted on the affected part, an early treatment or cure will be made possible. Furthermore, since they securely adhere to the skin by the adhesion of the edge parts 6b of the adherent base material 6, they will not unexpectedly slip off.

Figure 5:
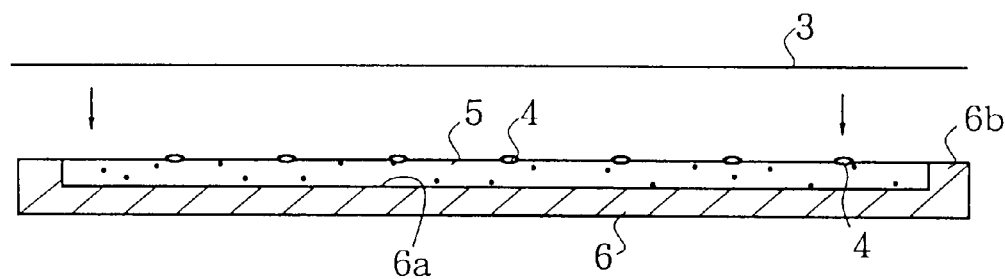
FIG. 5 is a cross-sectional view of a fifth preferred embodiment.

FIG. 5 shows a fifth preferred embodiment which is a combination of the third embodiment shown in FIG. 2 and the fourth embodiment shown in FIG. 4, wherein the parts which are identical to those in these embodiments are given the same reference numbers.

In this fifth preferred embodiment, concave parts 6a are formed on the adherent base material 6 and a kneaded substance 5 fills these concave parts 6a. The kneaded substance 5 is such that only a topicum is kneaded in a gelling agent. Chip-like materials 4 are disposed so that the surface thereof is exposed to the surface of the said kneaded substance 5. Therefore, this structure presents the actions of the third preferred embodiment in which the chip-like materials 4 are directly brought into contact with an affected part 4 and the actions of the fourth preferred embodiment in which the adherent base material 6 is securely brought into contact with the skin.

Figure 6:
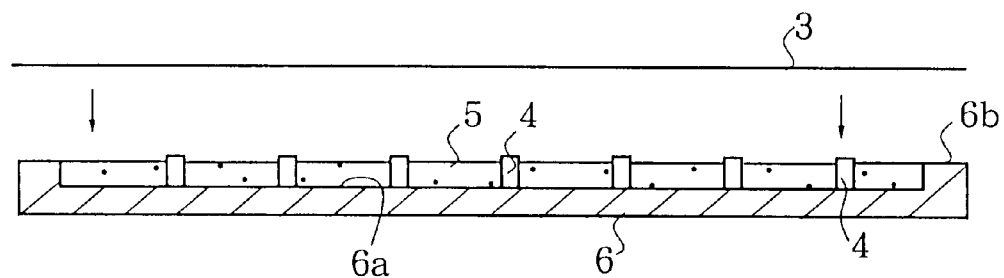
FIG. 6 is a cross-sectional view of a modified example of the fifth preferred embodiment.

FIG. 6 is a modified example of the fifth preferred embodiment. As shown in FIG. 3, this modified example utilizes slender titanium based materials 4. The lower end face of the titanium based material 4 is brought into contact with the upper surface of the concave parts 6a of the adherent base material 6, and these titanium based materials 4 are maintained to be erect by the adhesion of the concave parts 6a.

Therefore, even though a kneaded substance 5 in which a topicum is kneaded in a gelling agent is poured in the concave parts 6a, the kneaded substance will not slip off. This structure has both the actions of the structure shown in FIG. 3 and the actions of the structure shown in FIG. 5.

What is claimed is:

1. A poultice comprising a titanium based material selected from the group consisting of titanium itself, an inorganic titanium compound and a titanium alloy, and a pharmaceutically active ingredient which are kneaded and mixed with a gelling agent; wherein said poultice may be on a base material.

2. A poultice comprising: a kneaded substance in which a titanium based material selected from the group consisting of titanium itself, an inorganic titanium compound and a titanium alloy, and a pharmaceutically active ingredient are kneaded and mixed with a gelling agent; and a base material on one side of which said kneaded substance is laminated.

3. A poultice comprising: a kneaded substance in which a pharmaceutically active ingredient is kneaded and mixed with a gelling agent; a base material on one side of which said kneaded substance is laminated; and a titanium based material selected from the group consisting of titanium itself, an inorganic titanium compound and a titanium alloy, exposed on the surface of said kneaded substance.

4. A poultice comprising: a kneaded substance in which a titanium based material selected from the croup consisting of titanium itself, an inorganic titanium compound and a titanium alloy, and a pharmaceutically active ingredient are kneaded and mixed with a gelling agent; and an adherent substance which has concave parts, wherein said kneaded substance fills said concave parts.

5. A poultice comprising: a kneaded substance in which a pharmaceutically active ingredient is kneaded and mixed with a gelling agent; an adherent substance which has concave parts, wherein said kneaded substance fills said concave parts; and a titanium based material selected from the croup consisting of titanium itself, an inorganic titanium compound and a titanium alloy, exposed on the surface of said kneaded substance.

6. A poultice as set forth in claim 2, wherein the surface of said kneaded substance is covered with a film with a gas barrier property.

7. A poultice as set forth in claim 3, wherein the surface of said kneaded substance is covered with a film with a gas barrier property.

8. A poultice as set forth in claim 4, wherein the surface of said kneaded substance is covered with a film with a gas barrier property.

9. A poultice as set forth in claim 5, wherein the surface of said kneaded substance is covered with a film with a gas barrier property.

10. A poultice as set forth in claim 1, wherein the titanium based material is in the form of particles.

11. A poultice as set forth in claim 2, wherein the titanium based material is in the form of particles.

12. A poultice as set forth in claim 3, wherein the titanium based material is in the form of particles.

13. A poultice as set forth in claim 4, wherein the titanium based material is in the form of particles.

14. A poultice as set forth in claim 5, wherein the titanium based material is in the form of particles.

* * * * *